United States Patent [19]

Holtkamp, Sr.

[11] Patent Number: Plant 7,697

[45] Date of Patent: Oct. 29, 1991

[54] AFRICAN VIOLET PLANT NAMED LORETTA

[76] Inventor: Reinhold Holtkamp, Sr., Blumenstrasse 28, D 4242 Rees-Haffen, Fed. Rep. of Germany

[21] Appl. No.: 565,319

[22] Filed: Aug. 10, 1990

[51] Int. Cl.[5] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner

[57] ABSTRACT

A new and distinct cultivar of African violet named Loretta characterized by its double, purplish red flowers with slightly frilled, white edges; strong, upright flower stems that curve slightly toward the center to form a compact bouquet above the leaves; large, dark green, spear-shaped leaves; profuse flowering, vigorous and compact growth habit, flowering 10–11 weeks after potting, and its long lasting and non-dropping flowers.

1 Drawing Sheet

The present invention comprises a new and distinct cultivar of African violet plant, botanically known as *Saintpaulia ionantha*, and hereinafter referred to by the cultivar name Loretta.

The new cultivar was referred to during the breeding and selection process by the designation 282/43/69 and is a product of a planned breeding program. The new cultivar was originated from a cross made by me in the controlled breeding program in Haffen, Federal Republic of Germany. The female, or seed parent was a cultivar designated 2820. The male, or pollen parent was a cultivar designated 69/2.

Loretta was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Loretta has not been observed under all possible environmental conditions. The phenotype may vary significantly with variations in environment such as temperature, light intensity and day length. The following observations, measurements and values describe the new cultivar as grown in a 10 cm pot in Haffen, West Germany and Nashville, Tenn., under greenhouse conditions which closely approximate those generally used in commercial practice.

The following traits have been repeatedly observed and are determined to be basic characteristics of Loretta, which in combination distinguish this African violet as a new and distinct cultivar:

(1) Strong, upright flower stems curving slightly toward the center.

(2) Purplish red, double flowers with slightly frilled, white edges.

(3) Each plant carries 8–10 and more upright flower stems each of which carries 12–15 and more flowers.

(4) Long lasting, non-dropping flowers.

(5) Vigorous and compact grower.

(6) Plant saleable 10 to 11 weeks after potting.

(7) Seed capsules push slightly through.

(8) Large, dark green, spear-shaped leaves.

(9) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to the Royal Horticultural Society Colour Chart (R.H.S.), except where general colors of ordinary significance are referred to. Color values were taken under natural sunlight conditions at approximately 12 a.m. in Nashville, Tenn.

Botanical Classification: *Saintpaulia ionantha*, Ramat., c.v. Loretta

Parentage:

*Male parent.*—2820.

*Female parent.*—69/2.

Propagation: The new cultivar holds its distinguishing characteristics through successive propagations by leaf cuttings.

Plant: From 8 cm to 11 cm tall when grown in pots, and approximately 25–30 cm in diameter when fully grown.

Leaves:

*General form.*—Spear-shaped.

*Diameter.*—70–75 mm wide and 80–90 mm long.

*Texture.*—Velvety.

*Aspect.*—Very hairy, slightly shiny.

*Veins.*—Upperside: well visible; underside: well pronounced, light green, shiny.

*Color (upperside).*13 Yellow-Green Group 147 A and darker.

*Color (underside).*13 Greyed-Purple Group 186 A to B.

*Petiole.*—Strong upright, green with purplish brown touch, hairy.

Flowers:

*Buds.*—Bell-shaped, 7–9 mm just before opening, green with purplish red touch.

*Sepals.*—Five (5). Color: Purplish brown.

*Calyx.*—Shape: Almost flat. Aspect: Spear-shaped, hairy.

*Peduncle.*—Character: Strong upright, hairy. Color: Purplish brown.

Individual flowers:

*Size.*—35–40 mm.

*Shape.*—Double with slightly frilled edges.

*Color* (upperside).—Between Purple-Violet Group 80 A and Red-Purple Group 74 A, white edges. Under cooler temperatures and more intensive lighting, the purplish red tends to intensify.

*Color* (*underside*).—Purple-Violet Group 80 B to C.

*Borne.*—Each flower stem carries 12–15 and more flowers on strong, upright peduncles that are free standing above the leaves, thereby forming a compact bouquet.

*Flowering habit.*—Flowers 10–11 weeks after potting.

Reproductive organs:

*Stamens.*—Two (2). Anthers: 2 composed of 4 anther cells, seed capsule pushes slightly through.

*Filaments.*—Yellowish green with purplish red touch, 3–4 mm long.

*Pollen Color.*—Yellow Group 7 A.

*Styles.*—5–7 mm long, dark pink, base of ovary light green and hairy.

Roots: Normally developed, white when young, turning slightly brownish when older.

Disease Resistance: Up to date, Loretta has shown very good resistance to all major violet diseases.

General Observations: Loretta is very attractive due to its double purplish red flowers with slightly frilled, white edges. A tight bouquet of flowers free standing above the leaves develops after approximately 10–11 weeeks. Each of the 8–10 and more strong flower stems carries 12–15 and more round-looking flowers. The anthers are usually covered up. The flowers are long-lasting and non-dropping and the seed capsules push slightly through. Loretta is a vigorous and compact grower with large, dark green spear-shaped leaves.

I claim:

1. A new and distinct cultivar of African violet named Loretta, as described and illustrated, and particularly characterized by its double, purplish red flowers with slightly frilled, white edges; strong, upright flower stems that curve slightly toward the center to form a compact bouquet above the leaves; large, dark green, spear-shaped leaves; profuse flowering, vigorous and compact growth habit, flowering 10–11 weeks after potting, and its long lasting and non-dropping flowers.

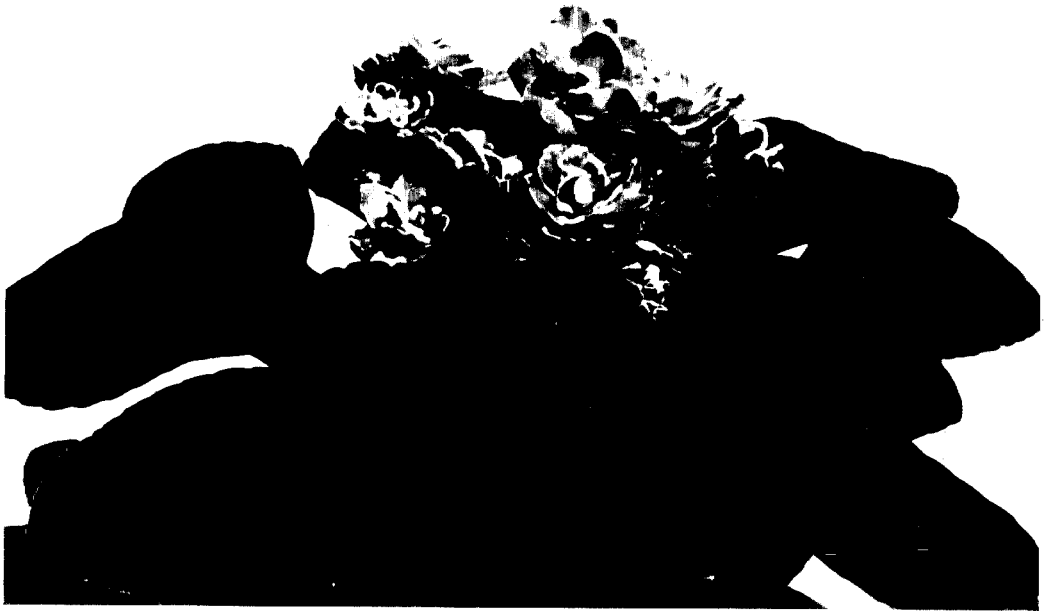

* * * * *